(12) United States Patent
Czajkowski et al.

(10) Patent No.: US 11,485,946 B2
(45) Date of Patent: Nov. 1, 2022

(54) DEVICE FOR STORING, INCUBATING OR MANIPULATING BIOLOGICAL SAMPLES AND METHOD FOR MOUNTING A HOLDER WITH A UV LIGHT SOURCE TO AN IRRADIATION CHAMBER OF SUCH DEVICE

(71) Applicant: Eppendorf AG, Hamburg (DE)

(72) Inventors: Paul Czajkowski, Bristol, CT (US); Erik Zamirowski, Longmeadow, MA (US)

(73) Assignee: Eppendorf AG, Hamburg (DE)

( * ) Notice: Subject to any disclaimer, the term of this patent is extended or adjusted under 35 U.S.C. 154(b) by 219 days.

(21) Appl. No.: 16/588,043

(22) Filed: Sep. 30, 2019

(65) Prior Publication Data

US 2021/0095237 A1    Apr. 1, 2021

(51) Int. Cl.
| | | |
|---|---|---|
| *B01L 9/06* | (2006.01) | |
| *C12M 3/00* | (2006.01) | |
| *C12M 3/06* | (2006.01) | |
| *C12M 1/00* | (2006.01) | |
| *G01N 1/38* | (2006.01) | |

(52) U.S. Cl.
CPC ............ *C12M 23/48* (2013.01); *B01L 9/06* (2013.01); *C12M 27/16* (2013.01); *C12M 31/08* (2013.01); *G01N 1/38* (2013.01); *B01L 2200/16* (2013.01); *B01L 2300/04* (2013.01); *B01L 2300/0809* (2013.01); *B01L 2300/0858* (2013.01); *B01L 2300/1883* (2013.01)

(58) Field of Classification Search
CPC ...... C12M 23/48; C12M 27/16; C12M 31/08; B01L 9/06; B01L 2200/16; B01L 2300/04; B01L 2300/0858; B01L 2300/1883; G01N 1/38

See application file for complete search history.

(56) References Cited

U.S. PATENT DOCUMENTS

| | | | |
|---|---|---|---|
| 4,141,060 A * | 2/1979 | Lackore | F21V 7/005 |
| | | | 362/213 |
| 10,379,044 B2 * | 8/2019 | Umetsu | G01N 21/41 |
| 2003/0040104 A1 * | 2/2003 | Barbera-Guillem | C12M 41/48 |
| | | | 435/286.2 |

(Continued)

OTHER PUBLICATIONS

Dewalt dw2535 3 Piece #6, #8, and #10 Countersink Assortment. Countersink Bits—Amazon.com. (Nov. 21, 2014) . Retrieved Sep. 22, 2021, from https://web.archive.org/web/20141121101400/http://www.amazon.com/DEWALT-DW2535-Piece-Countersink-Assortment/dp/B0000225OU. (Year: 2014).*

(Continued)

*Primary Examiner* — Samuel P Siefke
*Assistant Examiner* — Tingchen Shi
(74) *Attorney, Agent, or Firm* — Grogan, Tuccillo & Vanderleeden, LLP

(57) ABSTRACT

A device for storing, incubating or manipulating biological samples, in particular incubating device or shaking device, comprising a sample chamber, an irradiation chamber, and a holder with a UV light source, wherein a sidewall of the irradiation chamber comprises a first mounting member and wherein the holder comprises a second mounting member configured to interact with the first mounting member for pre-mounting the holder to the sidewall.

25 Claims, 11 Drawing Sheets

(56) References Cited

U.S. PATENT DOCUMENTS

| | | | |
|---|---|---|---|
| 2007/0264167 A1* | 11/2007 | Warner | A47G 23/0208 |
| | | | 422/400 |
| 2008/0279733 A1* | 11/2008 | Glazman | F24F 8/192 |
| | | | 422/243 |
| 2010/0232905 A1* | 9/2010 | Kempf | F16B 19/02 |
| | | | 411/500 |
| 2011/0277338 A1* | 11/2011 | Li | F26B 9/003 |
| | | | 34/275 |
| 2016/0083272 A1* | 3/2016 | Rajagopalan | C02F 1/325 |
| | | | 250/435 |
| 2019/0072853 A1* | 3/2019 | Van Der Post | G03F 7/70033 |
| 2019/0283029 A1* | 9/2019 | German | G01N 35/0099 |

OTHER PUBLICATIONS

Manfrotto 186 3/8-Inch Female to 5/8-Inch Stud 50mm Long Adapter—Replaces 3357, Aluminum, (n.d.). Retrieved Sep. 23, 2021, from https://www.amazon.com/Manfrotto-186-8-Inch-Female-Adapter/dp/B001M4HUHE/ref=psdc_3348261_t3_B072HFG4K3 (Year: 2021).*

* cited by examiner

DEVICE FOR STORING, INCUBATING OR MANIPULATING BIOLOGICAL SAMPLES AND METHOD FOR MOUNTING A HOLDER WITH A UV LIGHT SOURCE TO AN IRRADIATION CHAMBER OF SUCH DEVICE

TECHNICAL FIELD

The present invention relates to a device for storing, incubating or manipulating biological samples, in particular incubating device or shaking device, comprising a sample chamber, an irradiation chamber, and a holder with a UV light source.

Furthermore, the preset invention relates to a method for mounting a holder with a UV light source to an irradiation chamber of a device for storing, incubating or manipulating biological samples. Still further, the present invention relates to a holder for a device for storing, incubating or manipulating biological samples and to a set comprising an irradiation chamber and a holder.

DESCRIPTION OF RELATED ART

Devices for storing, incubating or manipulating biological samples are used in medical applications as well as scientific applications, for example in experimental work in molecular biology.

Incubating devices, or incubators, are devices to grow and maintain microbiological cultures or cell cultures. Incubators usually maintain optimal temperature, humidity and other conditions such as the CO, $CO_2$ and oxygen content of the atmosphere inside a sample chamber of the incubator.

A shaking device, or shaker, is a piece of laboratory equipment used to mix, blend or agitate substances in a tube or flask by shaking them. It is mainly used in the fields of medicine, chemistry and biology. A shaker may contain an oscillating board that is used to place the flasks, beakers or test tubes. A shaker is often configured as a particular embodiment of a device for storing, incubating or manipulating biological samples, wherein the oscillating board is arranged in a sample chamber controlled for e.g. temperature, humidity, oxygen and $CO_2$ content.

In medical, chemical and biological applications the air inside devices for storing, incubating or manipulating biological samples is often required to be free of contamination from spores, bacteria, germs, microbes and the like.

For decontamination of the air inside the device the use of ultraviolet light is known in the art. Ultraviolet light, in particular short wave ultraviolet light with wavelengths between 100 nm and 280 nm, also known as UVC light, is an efficient disinfection means to kill or inactivate microorganisms by destroying nuclear acids and disrupting their DNA, leaving then unable to perform vital cellular functions.

However, when an UV light source is arranged inside the sample chamber of a device for storing, incubating or manipulating biological samples there is a risk that the biological samples of interest will also be destroyed or harmed by the UV light. Therefore, devices for storing, incubating or manipulating biological samples can have a separate irradiation chamber in addition to the sample chamber. The irradiation chamber is fluidically connected with the sample chamber to allow circulation of air from the sample chamber through the irradiation chamber and back into the sample chamber. Decontamination with UV light takes place in the irradiation chamber and the decontaminated air is recirculated into the sample chamber.

WO 2008/128360 A1 discloses a device for the storage and preparation of biological samples with a UV sterilization device having a UV lamp. The UV lamp is arranged in a dedicated partial space in which the usable microbes are not present, so that UV light cannot reach the usable microbes. This arrangement permits a substantial reduction of air-borne microbes in the circulating air, even during the intended operation of the device. The inner surfaces of the partial space comprise cross webs configured such that air-borne microbes attach to the said inner surfaces. The microbes attached to the surface of the cross webs are irradiated with UV light for decontamination.

In prior art replacement of a defective UV light source is tedious and can take a considerable amount of time of up to two hours. Furthermore, the installation of UV light sources in known devices requires many work steps, which are further complicated by the fact that UV light sources have to be handled very carefully and therefore require a high level of attention of the maintenance worker replacing the UV light source. In addition, in known devices for storing, incubating or manipulating biological samples UV light still can reach the sample chamber from the irradiation chamber because the UV light source is usually arranged close to the air circulation openings connecting the irradiation chamber with the sample chamber.

Thus, there exists a long felt need in the art for a device for storing, incubating or manipulating biological samples in which a UV light source can be quick and safely replaced and in which entry of light from the UV light source into the sample chamber is efficiently prevented.

Description of the Invention: Objective, Solution, Advantages

The present invention proposes a device for storing, incubating or manipulating biological samples, in particular incubating device or shaking device, comprising a sample chamber, an irradiation chamber, and a holder with a UV light source, wherein a sidewall of the irradiation chamber comprises a first mounting member and wherein the holder comprises a second mounting member configured to interact with the first mounting member for pre-mounting the holder to the sidewall.

The present invention further proposes a method for mounting a holder with a UV light source to an irradiation chamber of a device for storing, incubating or manipulating biological samples, in particular an incubating device or a shaking device, comprising the steps of
Pre-mounting the holder to a sidewall of the irradiation chamber with a first mounting member of the sidewall and a second mounting member of the holder,
Final mounting of the holder to the sidewall.

Still further, the present invention proposes a holder for an UV light source for a device for storing, incubating or manipulating biological samples.

The present invention further proposes a set comprising an irradiation chamber and a holder for an UV light source for a device for storing, incubating or manipulating biological samples.

BRIEF DESCRIPTION OF THE DRAWINGS

In the following, the present invention is being described based on preferred embodiments of the invention.

Figure 1:
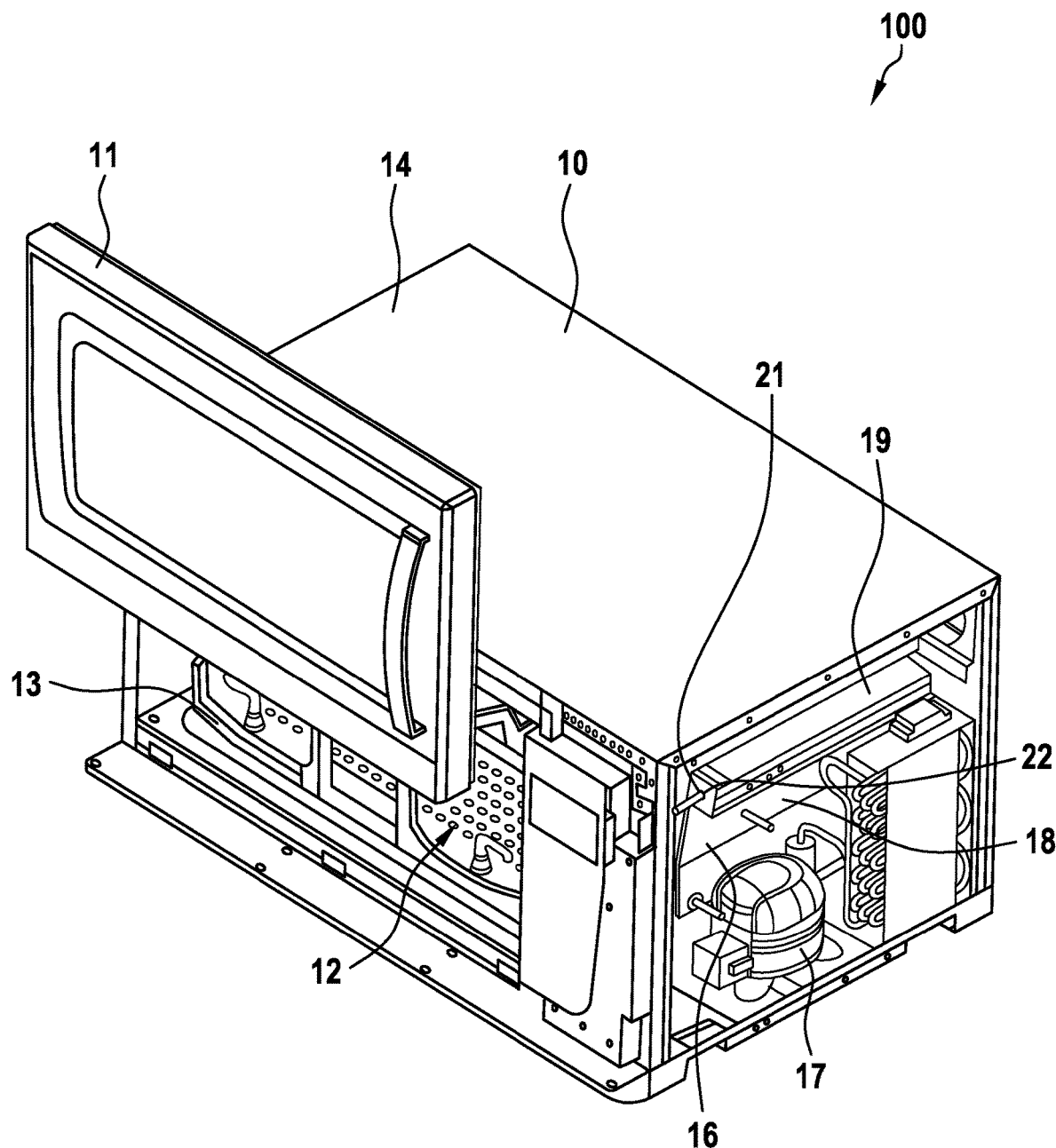
FIG. 1: shows a device for storing, incubating or manipulating biological samples.

The present invention proposes a device for storing, incubating or manipulating biological samples.

The device can be configured as an incubating device, or incubator, or as a shaking device, or shaker.

The device comprises a sample chamber in which biological samples can be stored, incubated or manipulated. In addition, the device comprises an irradiation chamber and a holder with a UV light source.

The UV light source is preferably configured to emit UV light, in particular UVC light with wavelengths between 100 nm and 280 nm, into the irradiation chamber for decontamination of air in the irradiation chamber.

Preferably, the irradiation chamber is fluidically connected to the sample chamber to allow air to circulate from the sample chamber through the irradiation chamber for decontamination and back into the sample chamber. For the fluidic connection openings may be provided in the irradiation chamber and sample chamber, respectively. In particular, each of the sample chamber and irradiation chamber may comprise respective entry and exit openings for air to enter or leave the sample chamber and the irradiation chamber.

The openings, in particular the entry and exit openings, may be covered with gratings to prevent UV light from exiting the irradiation chamber into the sample chamber.

To circulate the air through the sample chamber and the irradiation chamber fans may be provided, in particular in front of or close to the entry opening or the exit opening of the irradiation chamber.

In addition, the device may be configured for temperature and humidity control. Furthermore, the device may be configured for control of the CO, $CO_2$ or oxygen levels in the sample chamber.

The present invention proposes that a sidewall of the irradiation chamber comprises a first mounting member and that the holder comprises a second mounting member configured to interact with the first mounting member for pre-mounting the holder to the sidewall.

In particular, the second mounting member may be configured to interact with the first mounting member to form at least a first connection for pre-mounting the holder to the sidewall.

Pre-mounting in context of the present invention is to be understood as a partial or loose mounting of the holder to the sidewall, so that further steps are required for final mounting of the holder to the sidewall.

After pre-mounting the holder is held at the sidewall of the irradiation chamber by the interaction of the first mounting member and the second mounting member in such a way, that a worker mounting the holder to the sidewall can use both of his hands for final mounting the holder to the sidewall. The worker may thus unhand the holder when the holder is pre-mounted to the sidewall. He may then use both of his hands and possibly additional tools for final mounting of the holder to the sidewall.

In some embodiments the device for storing, incubating or manipulating samples is hermetically sealed, in particular sealed gastight. Preferably, the sample chamber and/or the irradiation chamber are hermetically sealed and/or sealed gastight.

Furthermore, the irradiation chamber and/or the holder may comprise openings so that UV light from the UV light source in the holder may exit the holder and enter the irradiation chamber through the openings.

In the final mounting position the holder may be mounted to the sidewall in a gastight manner, preferably to prevent microbes entering the irradiation chamber past the holder and through the openings in the holder and in the sidewall into the irradiation chamber. In the pre-mounting position the holder can be connected to the sidewall in a partial or loose connection, which may not be gastight.

The first mounting member and the second mounting member can be configured in any expedient way to allow an interaction between the first mounting member and the second mounting member for pre-mounting the holder to the sidewall.

Preferably, as described below in more detail, the first mounting member may be a stud and the second mounting member may be an aperture.

Alternatively or additionally, the first mounting member and the second mounting member may be configured as magnets or as a combination of a magnet and a magnetic element. For example, the first mounting member may be a magnetic section of the sidewall of the irradiation chamber and the second mounting member may be a magnet of the holder. Of course, the magnet and the magnetic element may be interchanged.

In a further alternative, the first mounting member and the second mounting member may be configured as adhesives or as a combination of an adhesive and a surface configured to interact with an adhesive. For example, the first mounting member may be a surface section of the sidewall configured to interact with an adhesive and the second mounting member may be an adhesive arranged on the holder. Of course, the adhesive and the surface configured to interact with the adhesive may be interchanged.

In some cases, the first mounting member and the second mounting member may be configured, preferably to form a second connection, for final mounting, in particular for fixing and immobilizing, the holder to the sidewall.

Thus, the first mounting member and the second mounting member may be configured to interact with each other to form both a first connection for pre-mounting the holder to the sidewall and to form a second connection for final mounting of the holder to the sidewall.

The first mounting member and the second mounting member may therefore have a double functionality. In a first function the first mounting member and the second mounting member form a first connection for pre-mounting the holder to the sidewall so that a worker can unhand the holder while the holder is partially or loosely held in place at the sidewall of the irradiation chamber and, in addition, the first mounting member and the second mounting member in a second function may be configured in such a way, that after the pre-mounting is established a final mounting may be obtained using the same first and second mounting members.

However, it is also possible that for forming a second connection for final mounting, in particular for fixing and immobilizing, the holder to the sidewall additional means, in particular a fixing member, may be provided. In this case, the first and the second mounting member are configured to form a first connection for pre-mounting the holder to the sidewall. A worker can then unhand the pre-mounted holder and use the fixing member for forming a second connection for final mounting, in particular for fixing and immobilizing, the holder to the sidewall.

Furthermore preferably, the holder is mountable and/or mounted to an outer face of the sidewall of the irradiation chamber.

By mounting or by configuring the holder to be mountable to an outer face of the sidewall of the irradiation chamber, installation or replacement of the holder comprising the UV light source is simplified.

In known devices for storing, incubating or manipulating biological samples the UV light source or a holder holding the UV light source is usually arranged on the inside of the irradiation chamber so that installation and replacement of the UV light source or the holder requires a worker to completely disassemble the incubating device and to open the irradiation chamber, which requires the use of special tools.

By mounting the holder to an outer face of the sidewall the time required for installation or replacement of the holder and the UV light source is shortened. In a particular preferred embodiment the holder and the UV light source held therein may be replaced by opening a side panel of the device to provide direct access to the outer face of the sidewall of the irradiation chamber. To install or replace the holder and the UV light source the maintenance worker simply has to open the side panel of the device. Then he can install or replace the holder quickly by first removing the holder to be replaced from the outer face of the sidewall and then attaching a new replacing holder to the outer face of the sidewall of the irradiation chamber by first pre-mounting the holder to the sidewall of the irradiation chamber using the first mounting member and the second mounting member and afterwards final mounting the holder to the sidewall of the irradiation chamber using either the first mounting member and the second mounting member or using an additional fixing member.

The holder may be configured as a box. The box may be shaped as a cuboid. The box may also be lightproof. Furthermore, the holder may be made from stainless steel or other materials.

Furthermore, it is preferred that the holder is thermally insulated. The holder can be thermally insulated using foam or other insulating material to make sure that the temperature regulated environment within the sample chamber and irradiation chamber is not affected by the holder or the UV light source loosing heat energy to the outside environment.

The holder may have integrated sensors to relay information back to an electronics assembly or to a printed circuit board. The sensors may be configured to monitor the light output of the UV light source.

The UV light source can be configured as a bulb and can be arranged inside the holder. The holder may have a hole for installing the bulb with a through hole fitting, which both seals a pass-thru wire to the UV light source and seals the hole of the box. The UV light source can have a connector on the outside of the box, which makes the entire module comprising the holder and the UV light source easy to disassemble and replace.

The box may furthermore be tapered in order to make it easier to fit into tight spaces.

Preferably, the first mounting member is a stud, in particular a pin, a peg or a standoff, and the second mounting member is an aperture for receiving the stud.

The stud may be arranged on an outer face of the sidewall of the irradiation chamber and the aperture for receiving the stud may be arranged in a flange or the like of the holder.

The person of ordinary skill will recognize, that for all preferred embodiments of the invention the stud and the aperture may be interchanged, so that the first mounting member is an aperture and that the second mounting member is a stud.

By entering the stud into the aperture, the stud and the aperture interact with each other, in particular to form a first connection, for pre-mounting the holder to the irradiation chamber, so that the holder is pre-mounted to the irradiation chamber in a partial or loose manner. In the pre-mounted state a worker can unhand the holder and use both of his hands and possibly additional tools for final mounting of the holder to the irradiation chamber.

The stud, in particular the pin, the peg or the standoff, may protrude from the outer face of the irradiation chamber at a right angle.

The stud may comprise a protrusion, preferably a head, configured to engage behind at least a section of a boundary of the aperture.

The aperture of the holder is bounded by a boundary of material of the holder. When the stud is entered into or received by the aperture the protrusion of the stud may engage behind at least a section of the boundary of the aperture. For example, the stud may comprise a head which has a larger diameter than at least a part of the aperture so that after entering the head of the stud into the aperture the head may engage behind a section of the boundary of said part of the aperture, which has a smaller diameter than the head. For the head to engage behind the section of the boundary of the aperture, a relative movement of the aperture and the stud may be required. The relative movement of the aperture and stud can be a result of a relative movement of the holder with respect to the irradiation chamber.

With the protrusion, in particular the head, engaging behind at least a section of a boundary of the aperture an accidental movement of the stud out of the aperture is prevented and, thus, the holder is held in a pre-mounted manner at the irradiation chamber so that the holder is held partially or loosely in place at the irradiation chamber.

It is also possible that the protrusion is an appendage protruding from the stud at preferably a right angle. Furthermore, the stud, in particular the pin, the peg or the standoff, may be arranged on the sidewall of the irradiation chamber in a rotatable manner. In this case, the stud comprising the protrusion, in particular the appendage, is first aligned with the aperture so that the stud comprising the appendage can be entered into and received by the aperture. Afterwards, the stud or the pin may be rotated such that the appendage engages behind at least a section of the boundary of the aperture tier pre-mounting the holder to the irradiation sidewall chamber. If the stud in particular the pin, the peg or the standoff, is arranged rotatably on the sidewall of the irradiation chamber precautions may have to be taken so that no outside air enters the irradiation chamber through a receptacle for the stud on the sidewall of the irradiation chamber.

It is furthermore preferred that the aperture is a countersunk aperture.

Also, it is possible that the section of the boundary of the aperture comprises an inclined plane configured such that a relative movement of the inclined plane and the protrusion of the stud engaging behind the inclined plane creates mechanical advantage to tighten the holder against the sidewall.

For pre-mounting the holder to the irradiation chamber the stud comprising the protrusion is entered into or received by the aperture. The holder comprising the aperture is preferably displaced laterally with regard to the irradiation chamber in such a way that the protrusion of the stud engages behind the inclined plane of the section of the boundary of the aperture. By further displacing the holder laterally the protrusion of the stud slides along the inclined plane in the rising direction of the inclined plane, thereby creating a mechanical advantage to tighten the holder against the sidewall. In the rising direction the thickness of the material of the section of the boundary defining the inclined plane increases. By tightening the holder against the sidewall the holder is pre-mounted and partially secured to the irradiation chamber, preventing the holder to be accidentally removed from the sidewall of the irradiation chamber. The pre-mounted holder is reliably held at the irradiation chamber allowing a worker to unhand the holder without the risk of the holder accidentally separating from the sidewall of the irradiation chamber.

A relative movement of the inclined plane and the stud comprising the protrusion may also be effected in case of a rotatable stud by rotating the stud such that the protrusion engages behind the inclined plane. In this case, the inclined plane is preferably configured as a circular section of the boundary of the aperture.

In addition, the aperture may be configured as a keyhole.

The keyhole may have a, preferably circular, entry section for receiving the protrusion of the stud and a slide section adjacent to the entry section. Furthermore, a width of the slide section may be smaller than a dimension of the protrusion of the stud. Said width of the slide section may also be larger than a diameter of a neck part of the stud, so that the neck part can freely enter the slide section by a relative movement of the holder with respect to the irradiation chamber, i.e. of the aperture with respect to the stud. When the protrusion has a larger dimension than the width of the slide section it can easily engage behind a boundary of the slide section. The width of the slide section may be measured at a right angle to the direction of longest extension of the slide section.

Preferably, the stud and the keyhole are configured such that upon receiving the protrusion of the stud through the entry section a relative movement of the stud and the keyhole enters the stud, in particular a neck part of the stud, into the slide section so that the protrusion engages behind a boundary of the slide section.

The keyhole may be configured in any expedient manner. It may only be required that the keyhole comprises an entry section and an adjacent slide section, wherein the entry section has dimensions allowing the protrusion of the stud to be guided through the entry section and wherein at least one dimension of the slide section is smaller than the diameter of the protrusion so that the protrusion can engage behind a section of the boundary of the slide section.

The boundary of the aperture comprising the inclined plane may be a boundary of the slide section. Thus, after the stud comprising the protrusion has been entered into the aperture through the entry section a first lateral displacement of the holder relative to the irradiation chamber results in the protrusion to engage behind a section of the boundary of the slide section comprising the inclined plane. A further lateral displacement of the holder creates a mechanical advantage between the protrusion of the stud and the inclined plane to tighten the holder to the sidewall of the irradiation chamber.

It is furthermore possible that the first mounting member and the second mounting member form at least one of a clip connection and a snap fit connection.

For example, by entering the protrusion of the stud into the entry section of the keyhole and by displacing the holder laterally so that the protrusion engages behind a section of the boundary of the slide section a pre-mounting of the holder to the sidewall of the irradiation chamber is achieved. With a further lateral displacement of the holder with regard to the irradiation chamber in the same direction the second mounting member and the first mounting member may form a clip connection or a snap fit connection, which further safeguards against an accidental loosening of the pre-mounting.

It is possible that the boundary of the slide section of the keyhole comprises an indentation, in particular a notch or a groove, at a distal end from the entry section for receiving at least part of the protrusion, for example a bulge, to form the clip connection or snap fit connection. The holder can be displaced laterally relative to the irradiation chamber so that the protrusion or head of the stud engages behind a boundary section of the slide section. With a further lateral displacement of the holder an end position of the holder is reached, in which at least part of the protrusion engages the indentation at the distal end of the slide section, thereby creating a snap fit connection or clip connection, which prevents a displacement of the protrusion or head in the opposite direction along the slide section.

Alternatively or additionally the protrusion, in particular the head, of the stud may have a slightly larger diameter than the aperture, in particular than the entry section of the aperture. Thus, for entering the protrusion of the stud into the entry section or the aperture a small force may have to be exerted to elastically deform the protrusion allowing it to fully pass through the aperture or the entry section of the aperture. After the head or the protrusion has passed through the aperture the protrusion relaxes and engages behind a section of the boundary of the aperture. To remove the holder from the irradiation chamber a small force is required to pull the stud comprising the protrusion out of the aperture.

The clip connection or the snap fit connection may be part of a first connection for pre-mounting the holder to the irradiation chamber, i. e. the snap fit connection or the clip connection does not provide a gas tight or hermetically sealed connection between the holder and the sidewall of the irradiation chamber.

However, it is also possible that the snap fit connection or clip connection formed by the first mounting member and the second mounting member establishes or forms a second connection for final mounting the holder to the irradiation chamber.

One of ordinary skill in the art will understand that the indentation, notch or groove may be arranged in the protrusion or head of the stud and that the slide section comprises at the distal end from the entry section a bulge or the like, which is configured to engage in the indentation of the protrusion or head after a sufficient lateral displacement of the holder.

While the snap fit or clip connection provided by the first mounting member and the second mounting member may already provide the second connection for final mounting of the holder to the sidewall of the irradiation chamber it is also possible that the snap fit connection or the clip connection only provides the first connection for pre-mounting the holder to the sidewall of the irradiation chamber.

In any case a further fixing member may be provided, which is configured for final mounting, in particular for fixing and immobilizing, the holder to the irradiation chamber.

Preferably the fixing member is a screw, the holder comprises a hole and the sidewall comprises a threaded hole for receiving the screw.

Thus, for mounting the holder to the sidewall of the irradiation chamber first the holder is pre-mounted to the sidewall using the first mounting member and the second mounting member. For example, a head or protrusion of a stud on a sidewall of the irradiation chamber is guided through an aperture, in particular an entry section of a keyhole, of the holder and then the holder is displaced laterally with regard to the irradiation chamber, so that the head or the protrusion engages behind an inclined plane on a boundary section of the aperture, in particular of a slide section of a keyhole. When the holder is pre-mounted to the irradiation chamber a fixing member, in particular a screw, is used for final mounting of the holder. If the fixing member is a screw, the screw is guided through a hole of the holder into a threaded hole of the sidewall.

By tightening the screw the holder is further tightened to the sidewall and the second connection between the holder and the sidewall of the irradiation is established. The second connection may be configured as a gas tight or hermetically sealed connection between the holder and the irradiation chamber.

Preferably a seal is arranged between a contact surface of the holder and the sidewall of the irradiation chamber.

The seal may be configured as a rope seal or sealing cord.

If the aperture is configured as a keyhole with an entry section and a slide section, wherein a boundary of the slide section comprises an inclined plane, a lateral displacement of the holder engages the head or protrusion of the stud behind the inclined plane of the slide section of the keyhole. A further lateral displacement in the same direction creates a mechanical advantage between the protrusion or head and the inclined plane to tighten the holder to the irradiation chamber, thereby compressing the seal arranged between a contact surface of the holder and the sidewall of the irradiation chamber. By compressing the seal a hermetically sealed or gas tight connection between the holder and the irradiation chamber can be provided.

If the first mounting member and the second mounting member are configured to form both of a first connection for pre-mounting the holder to the sidewall and a second connection for final mounting of the holder to the sidewall, the compression of the seal between the contact surface of the holder and the sidewall of the irradiation chamber may be sufficient to provide a gas tight or hermetic seal between the holder and the irradiation chamber.

If the first mounting member and the second mounting member are only configured to form a first connection for pre-mounting the holder to the irradiation chamber the compression of the seal between the contact surface of the holder and the sidewall of the irradiation chamber may not be sufficient to provide a gas tight or hermetic seal. In this case, a further fixing member, for example a screw, may be required to form a second connection for a final mounting of the holder to the irradiation sidewall.

If the fixing member is a screw, tightening the screw results in a further compression of the seal so that the holder and the irradiation chamber are hermetically or gas tight sealed against the surroundings.

Further preferably the seal is at least one of a foam seal, a urethane seal and a self lubricating seal.

If the seal or the rope seal or the sealing cord is a self-lubricating seal shearing forces on the seal disposed between the contact surface of the holder and the sidewall of the irradiation chamber caused by the lateral displacement of the holder with regard to irradiation chamber can be minimized.

However, it is also possible to lubricate the seal before pre-mounting the holder to the irradiation chamber.

Preferably at least one, especially preferably both, of the sidewall of the irradiation chamber and the holder comprises an opening to allow light from the UV light source in the holder to enter the irradiation chamber when the holder is attached to the irradiation chamber.

In the final mounting position the opening in the sidewall of the irradiation chamber and the opening in the holder are arranged on top of each other so that light from the UV light source can enter the irradiation chamber.

Furthermore preferably, at least one of the sidewall of the irradiation chamber and the holder comprises a slit for focusing light from the UV light source into the irradiation chamber.

The slit may be either the opening in the sidewall of the irradiation chamber or the opening in the holder.

Furthermore, it is preferred that the irradiation chamber comprises in the interior a reflector for reflecting UV light from the UV light source.

It is particularly preferred that the light from the UV light source is focused by the slit onto the reflector. The reflector is configured for reflecting the UV light back. By reflecting the UV light the intensity of the light is amplified to improve disinfection or decontamination of the air inside the irradiation chamber.

Preferably, the reflector is mounted to an inner face of the sidewall by at least one distance piece.

Furthermore preferably, the reflector is mounted opposite to the opening in the sidewall and/or the holder or opposite to the slit in the holder and/or in the sidewall so that light entering the irradiation chamber from the UV light source is focused on the reflector.

It is also preferable that the reflector has a curved configuration. A curved reflector focuses the UV light to make the decontamination or disinfection more effective.

Particularly preferably, the reflector has a cylindrical configuration and the UV light and/or the slit is further preferably positioned in the central axis of the cylindrical configuration of the reflector.

Thus, UV light from the UV light source is reflected by the reflector right back onto the slit or onto the UV light source itself, thereby preventing or minimizing UV light being scattered through the irradiation chamber and possibly entering the sample chamber.

Preferably, the reflector and an inner face of the sidewall of the irradiation chamber define a passageway for air.

In particular, if the reflector is mounted to an inner face of the sidewall with at least one distance piece a passageway for air is defined between the reflector and the inner face of the sidewall of the irradiation chamber.

The passage way for air is configured such that either all or at least part of the air flow in the irradiation chamber flows through the passageway for disinfection of all or part of the air.

Preferably at least one lateral edge of the reflector is at a distance from the inner face of the sidewall for forming at least one of an entry and an exit for air into or out of the passageway.

Particularly preferred at least two lateral edges of the reflector are at a distance from the inner face of the sidewall. A first lateral edge and the inner surface form an entry for air into the passage way and an opposite second lateral edge and the inner surface of the sidewall form an exit for air out of the passageway.

The present invention also proposes a method for mounting a holder with a UV light source to an irradiation chamber of a device for storing, incubating or manipulating biological samples, in particular an incubating device or a shaking device. The method comprises the steps of Pre-mounting the holder to a sidewall of the irradiation chamber with a first mounting member of the sidewall and a second mounting member of the holder, and Final mounting of the holder to the sidewall.

The method is particularly suited for a device for storing, incubating or manipulating biological samples as described above.

In the step of pre-mounting the holder to a sidewall of the irradiation chamber with the first mounting member of the sidewall and the second mounting member of the holder, the holder is partially or loosely mounted to the sidewall of the irradiation chamber so that a worker can unhand the holder to conduct the final mounting step with both of his hands and possibly with a use of additional tools.

Preferably the first mounting members a stud arranged on the sidewall of the irradiation chamber comprising a protrusion, in particular a head, and the second mounting member is a keyhole in the holder.

Furthermore preferably, the method comprises the steps of:

Guiding the protrusion of the stud through an entry section of the keyhole in the holder, Displacing the holder laterally so that a neck part of the stud enters a slide section of the keyway and the protrusion engages behind a boundary of the slide section to pre-mount a holder to the sidewall and Fixing or immobilizing the holder in position with a fixing member.

The sideways movement or lateral displacement of the holder is particularly preferably at a right angle to the movement for guiding the protrusion of the stud through the entry section of the keyhole.

The slide section may comprise an inclined plane at a boundary, the method further comprising the step:

Creating a mechanical advantage by displacing the holder laterally and engaging the protrusion behind the inclined plane to tighten the holder against the sidewall.

Still further preferably, a seal is arranged on at least one of a contact surface of the holder and the sidewall of the irradiation chamber, the method further comprising the step of lubricating the seal.

Furthermore, the present invention proposes a holder for an UV light source for a device for storing, incubating or manipulating biological samples as described above.

In addition, a set comprising an irradiation chamber and a holder for a device for storing, incubating or manipulating biological samples according to the above described embodiments is proposed.

PREFERRED EMBODIMENTS OF THE INVENTION

Figure 2:
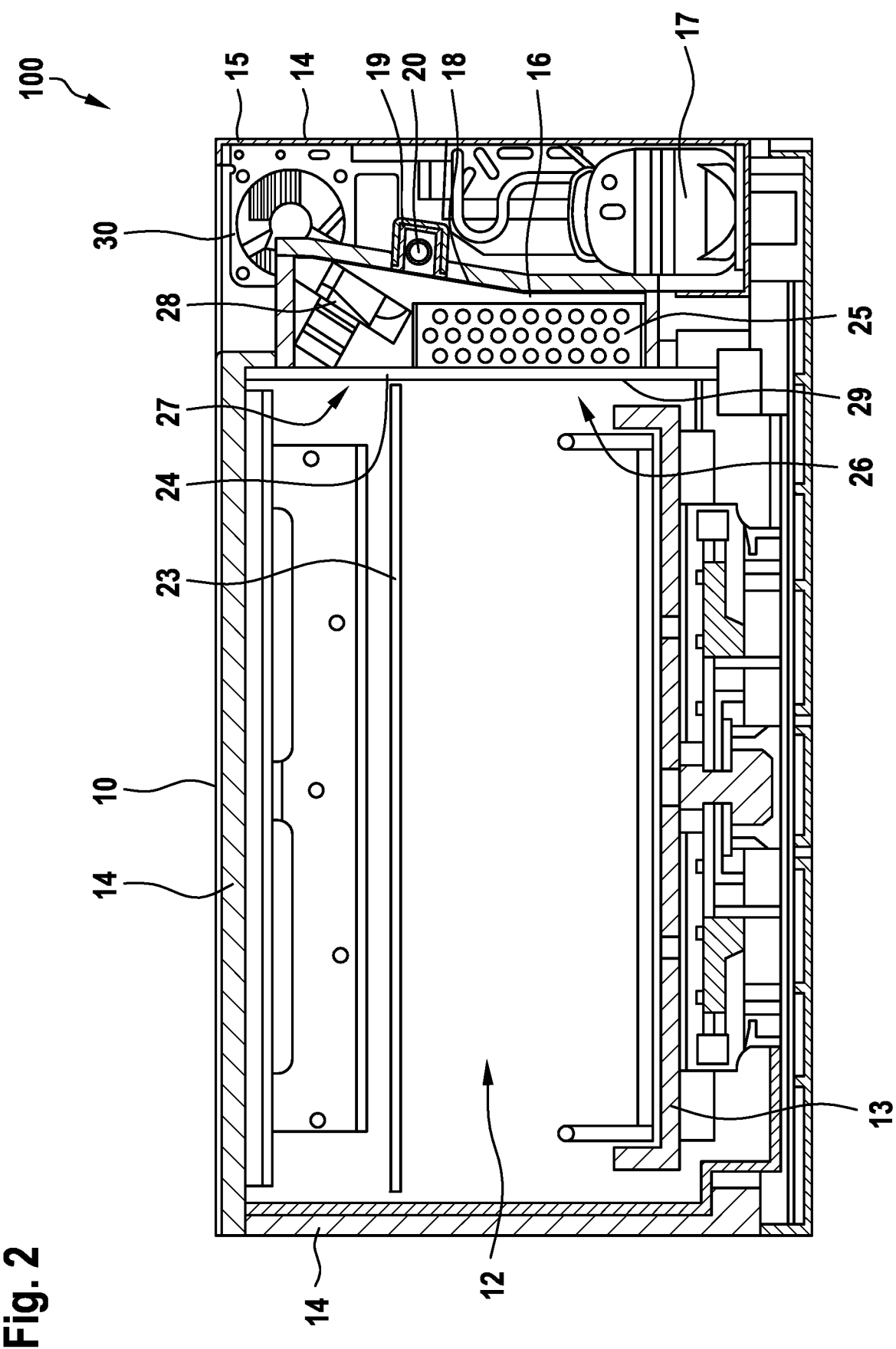
FIG. 2: shows a cross section through a device for storing, incubating or manipulating biological samples.

FIGS. 1 and 2 show a device 100 for storing, manipulating or incubating biological samples. FIG. 1 is a perspective view of the device 100. FIG. 2 is a cross sectional view of device 100.

Device 100 comprises a casing 10 and a front door 11. The device 100 further comprises a sample chamber 12. An oscillating board 13 for placing flask, beakers or test tubes is disposed inside sample chamber 12. The device 100 is shown in FIG. 1 with front door 11 in an open position. The casing 10 comprises panels 14. A side panel 15 (shown in FIG. 2) is removed from the device 100 as shown in FIG. 1 to provide access to an irradiation chamber 16 and to a refrigeration or heating module 17. On a sidewall 18 of the irradiation chamber 16 a holder 19 is arranged. A UV light source 20 is located inside holder 19 (FIG. 2). Holder 19 is approximately cuboid sized and comprises a hole 21 with a through-hole fitting 22 to seal the hole 21. As shown in FIG. 2 the sample chamber 12 comprises the oscillating board 13 and an additional shelf 23.

The irradiation chamber 16 is attached to a wall 24 of the sample chamber 12 and has a tapered configuration. A heat exchanger 25 of the refrigeration or heating module 17 is arranged inside irradiation chamber 16. The irradiation chamber 16 further comprises an entry opening 26 and an exit opening 27 to circulate air through the sample chamber 12 and the irradiation chamber 16. Air from the sample chamber 12 enters the irradiation chamber through entry opening 26 and leaves the irradiation chamber 16 through exit opening 27 back into the sample chamber 12. For driving the air circulation, a fan 28 is arranged inside the irradiation chamber 16. The entry opening 26 and the exit opening 27 are covered with gratings 29 to prevent UV light from exiting the irradiation chamber 16 and entering the sample chamber 12.

Figure 3:
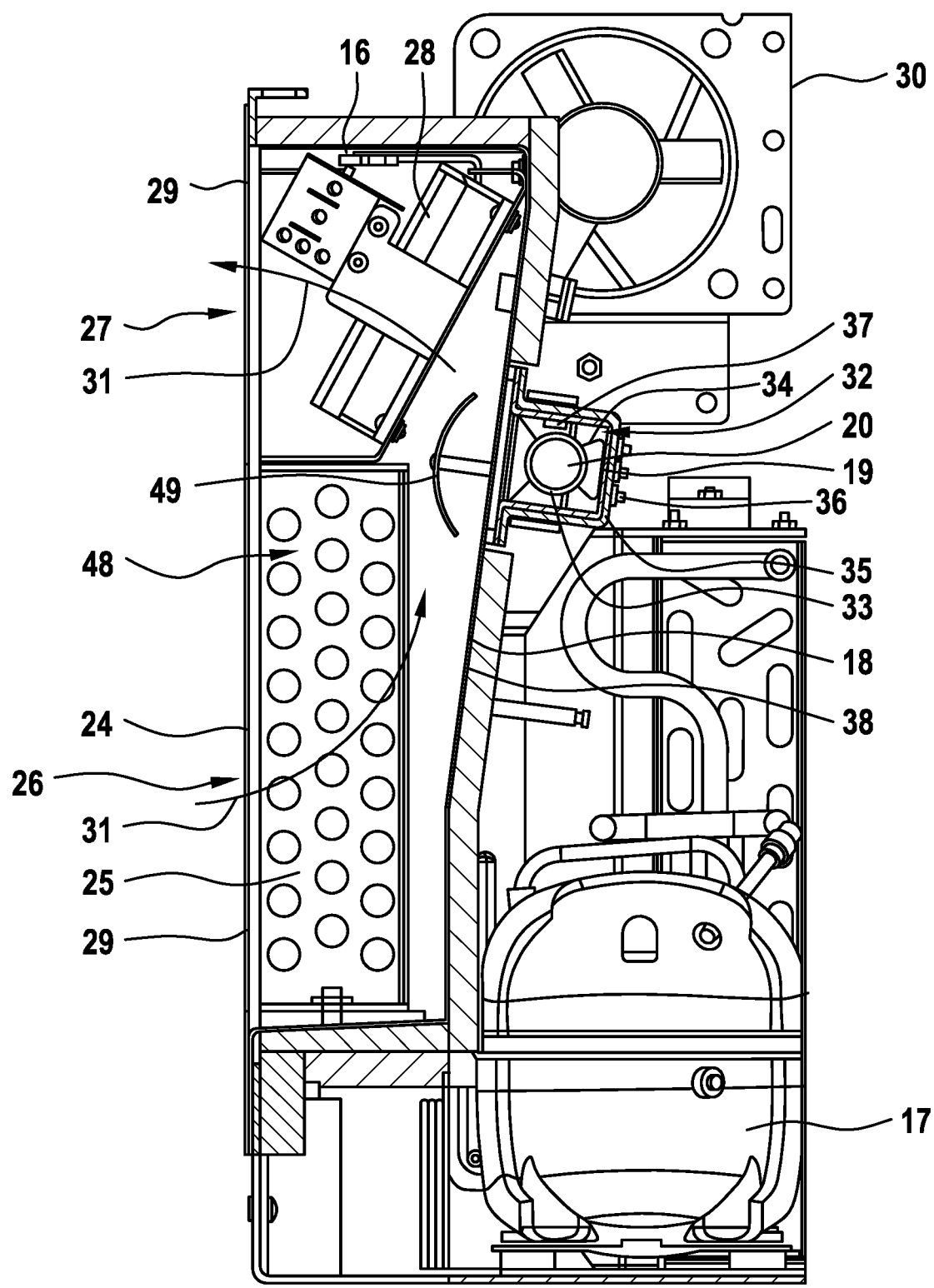
FIG. 3: shows an irradiation chamber and a holder with a UV light source.
Figure 4:
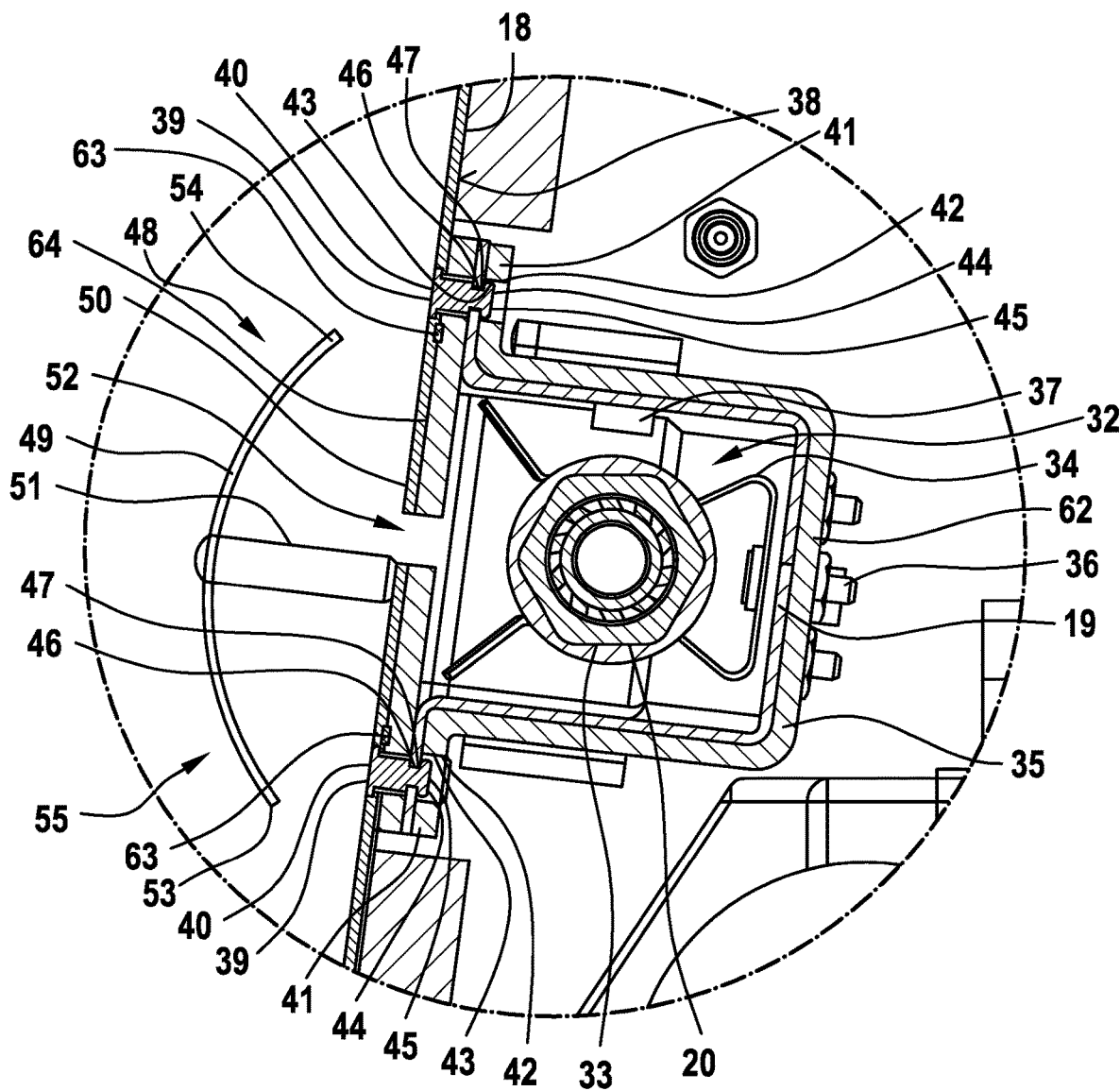
FIG. 4: shows a detail view of an irradiation chamber and a holder with a UV light source.

FIG. 3 is a cross sectional view through irradiation chamber 16. FIG. 4 is a detail view of the upper part of the irradiation chamber 16 of FIG. 3.

Irradiation chamber 16 is arranged at wall 24 of the sample chamber 12 in close proximity to the refrigeration or heating module 17. For removing heat from the refrigeration or heating module 17 an outer fan 30 is provided. Inside irradiation chamber 16 a heat exchanger 25 is arranged as well as fan 28 for driving air circulation through the irradiation chamber 16. Air from the sample chamber 12 enters the irradiation chamber through entry opening 26 and leaves the irradiation chamber 16 through exit opening 27. The airflow 31 is indicated with arrows. Holder 19 is attached to sidewall 18 of irradiation chamber 16. In an interior space 32 of holder 19 a bulb 33 of the UV light source 20 is arranged. The bulb 33 is held in holder 19 with a clip 34. Clip 34 is attached to a wall 35 of holder 19 with a screw connection 36. Inside interior space 32 a UVC light sensor 37 is arranged for monitoring the light output of the UV light source 20. Holder 19 is attached to an outer face 38 of sidewall 18 of irradiation chamber 16.

As shown in FIG. 4 sidewall 18 of irradiation chamber 16 comprises studs 39 protruding at a right angle from the sidewall 18. Each stud 39 is a first mounting member 40. Holder 19 comprises flanges 41 with second mounting members 42 configured as apertures 43 for receiving studs 39. The studs 39 further comprise protrusions 44, which are configured as heads 45. Heads 45 of studs 39 are guided through and received in apertures 43 and engage behind a section 46 of a boundary 47 of the apertures 43.

In an interior 48 of irradiation chamber 16 a reflector 49 is arranged on an inner face 50 of sidewall 18. The reflector 49 is configured cylindrically and attached to the inner face 50 with a distance piece 51. UV light emitted by UV light source 20 is focused through a slit 52 onto reflector 49. Light emitted by the UV light source 20 enters the irradiation chamber through slit 52 and is reflected back onto slit 52 by reflector 49.

Reflector 49 comprises a first lateral edge 53 and a second lateral edge 54. Reflector 49 comprising first lateral edge 53 and second lateral edge 54 is arranged at a distance from the inner face 50 of sidewall 18, thereby defining a passageway 55 between inner face 50 and reflector 49 for air to be decontaminating using the UVC light from the UV light source 20. As shown in FIG. 3 Reflector 49 is positioned at a second distance from wall 24 opposite to sidewall 18, so that only a part of the air circulating through irradiation chamber 16 passes through the passageway 55. In alternative embodiments, the reflector 49 may be arranged on wall 24 so that all of the air circulating through irradiation chamber 16 is guided through passageway 55.

FIGS. 5 to 9 show the irradiation chamber 16.

Figure 5:
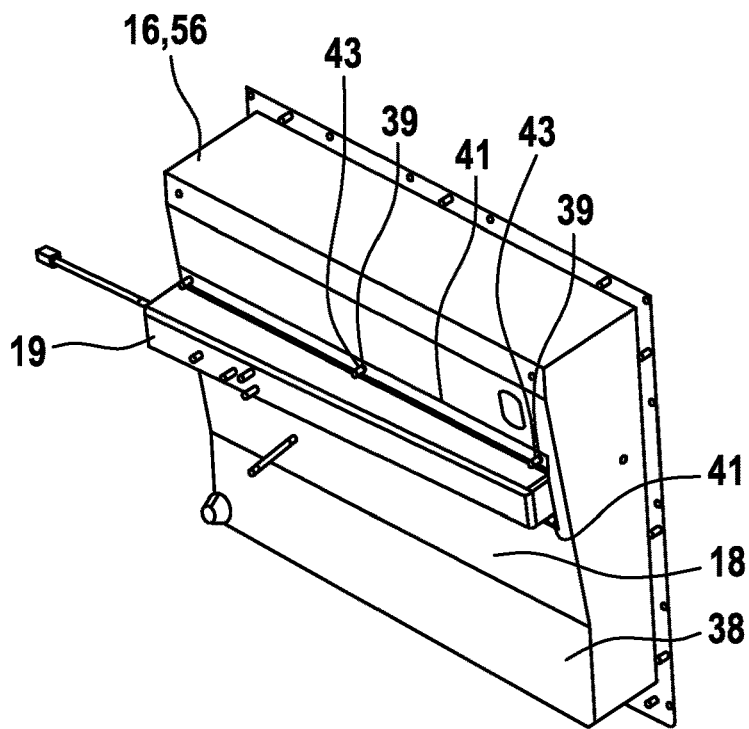
FIG. 5: shows a first perspective of an irradiation chamber.
Figure 6:
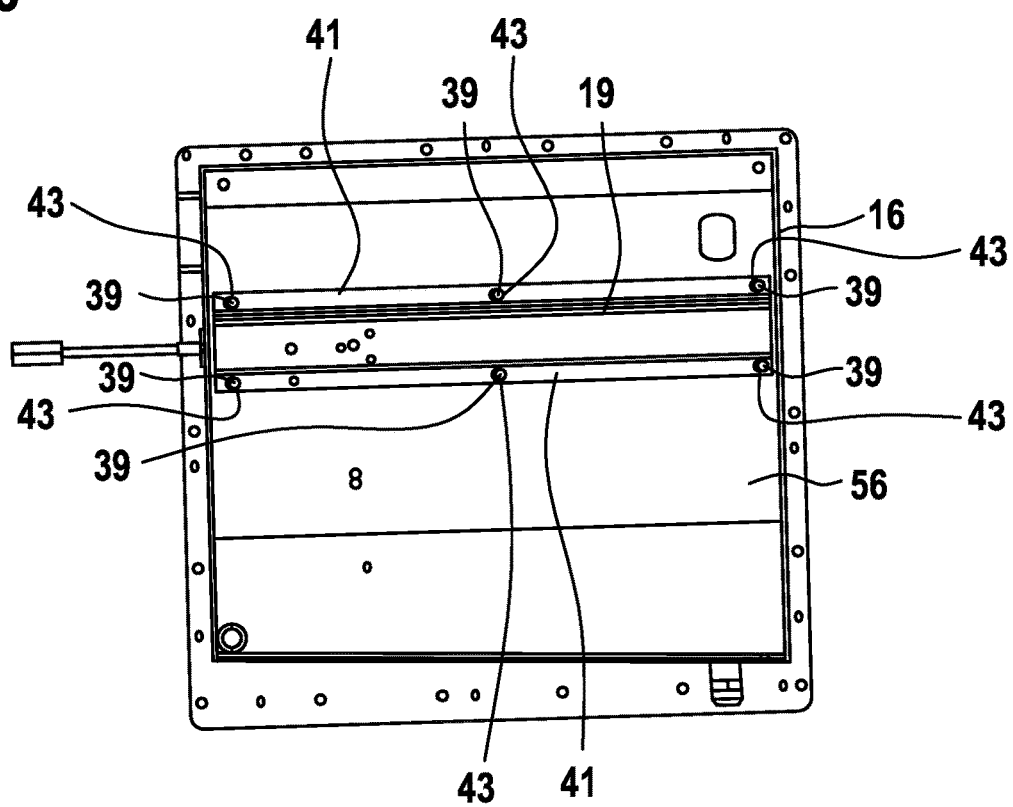
FIG. 6: shows a second perspective of an irradiation chamber.
Figure 7:
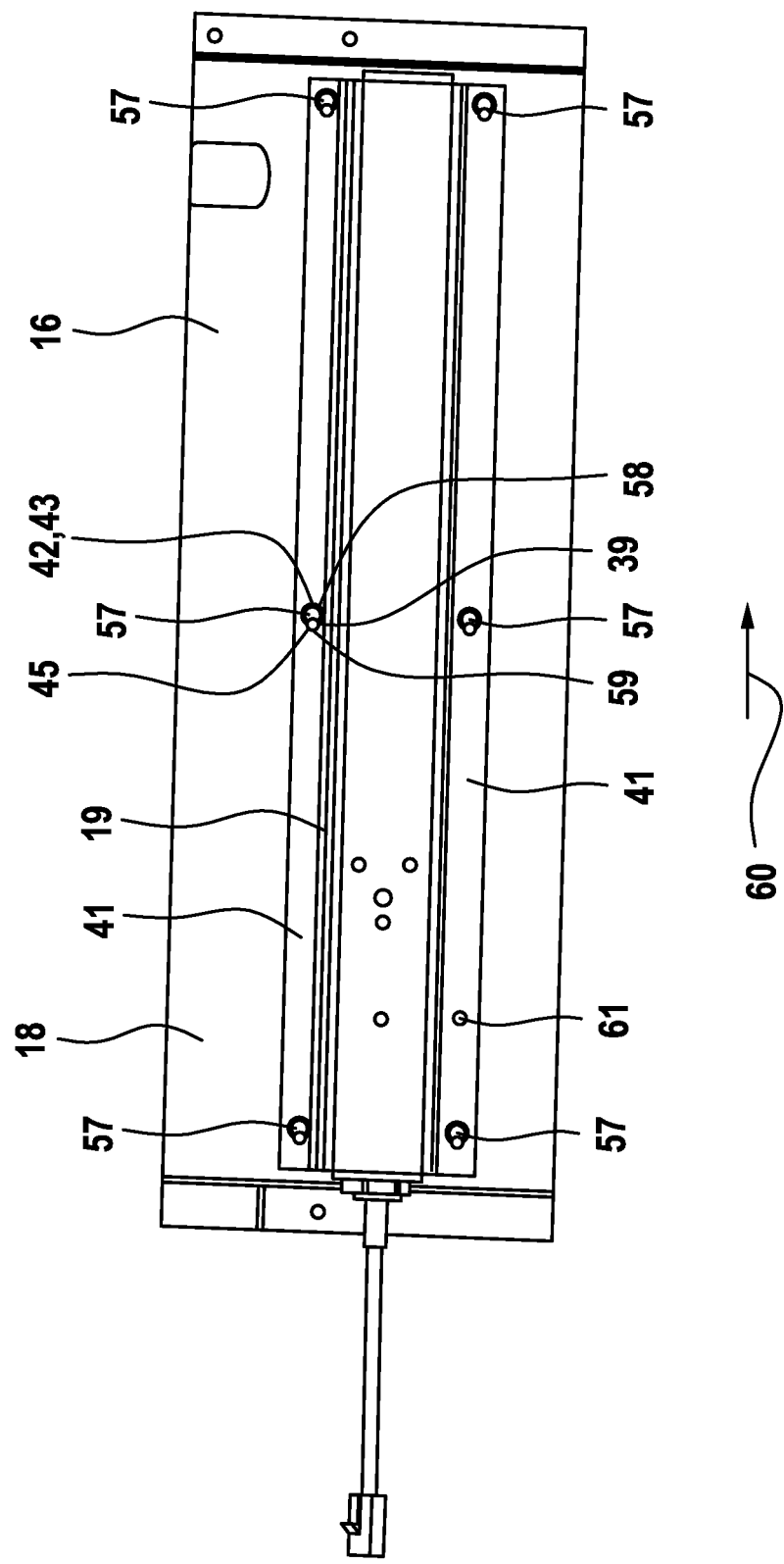
FIG. 7: shows a third perspective of an irradiation chamber.

FIG. 5 shows a perspective view of the irradiation chamber 16. The irradiation chamber 16 comprises a cover 56 comprising the sidewall 18. Holder 19 is attached to outer face 38 of sidewall 18 and has a tapered configuration to fit into tight spaces. Holder 19 is attached to sidewall 18 with studs 39 of irradiation chamber 16 guided through apertures 43 in flanges 41 of holder 19. FIG. 6 is a side view of irradiation chamber 16, showing holder 19 attached to sidewall 18 with studs 39 and apertures 43. FIG. 7 is a detail view of FIG. 6 of the holder 19 attached to sidewall 18 of irradiation chamber 16. Holder 19 comprises flanges 41. In each flange 41 second mounting members 42 configured as apertures 43 are arranged. Apertures 43 are shaped as keyholes 57 comprising an entry section 58 and a slide section 59 adjacent to entry section 58. In total, holder 19 comprises six keyholes 57. For pre-mounting holder 19 to sidewall 18 of irradiation chamber 16, heads 45 of studs 39 are guided through entry sections 58. Afterwards, a displacement of holder 19 in a lateral direction 60 results in head 45 engaging behind a section 46 of boundary 47 of keyholes 57, as shown in FIG. 4. In the position shown in FIG. 7, holder 19 is pre-mounted at irradiation chamber 16. Thus, holder 19 is partially or loosely held in place by the heads 45 engaging behind sections 46 of boundaries 47 of keyholes 57. For a final mounting, a screw as a fixing member is guided through a hole 61 in flange 41 of holder 19. The screw is received in a corresponding threaded hole in sidewall 18 of irradiation chamber 16. By tightening the screw, holder 19 is drawn to sidewall 18 and fixed to irradiation chamber 16.

Figure 8:
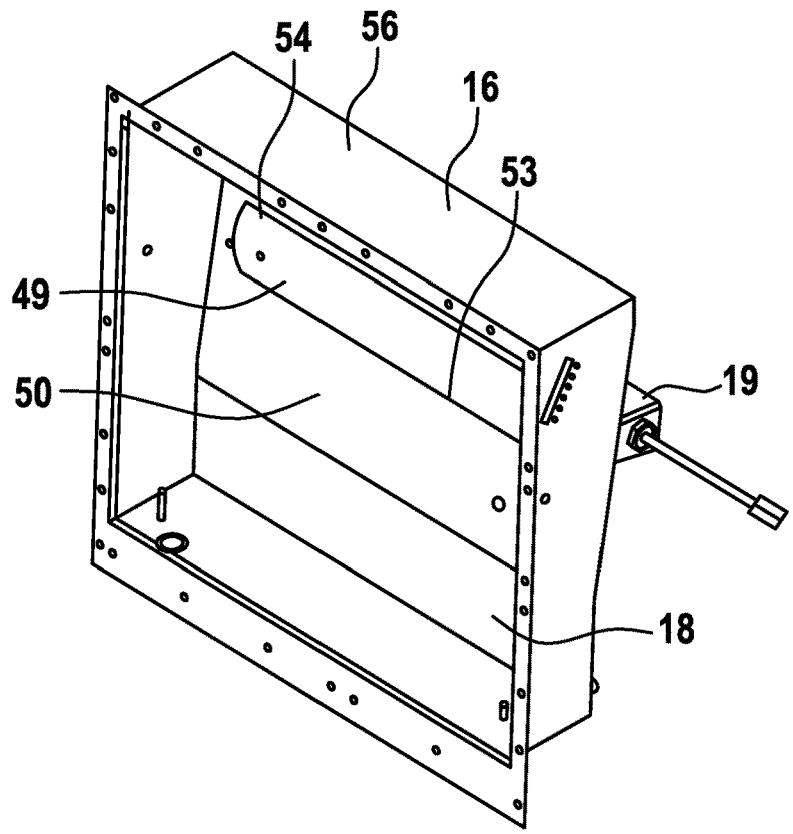
FIG. 8: shows a fourth perspective of an irradiation chamber.
Figure 9:
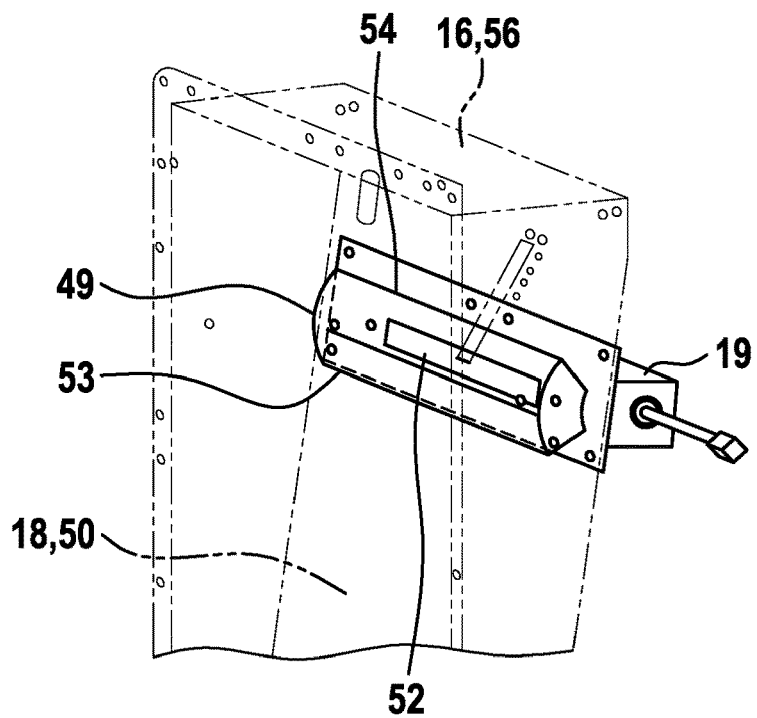
FIG. 9: shows a semi-transparent fifth perspective of an irradiation chamber.

FIG. 8 shows another perspective view of cover 56 of irradiation chamber 16. Reflector 49 is attached to inner face 50 of sidewall 18, opposing holder 19. FIG. 9 is a semi-transparent drawing of the upper part of cover 56 according to FIG. 8. As shown in FIG. 9 sidewall 18 of irradiation chamber 16 comprises a slit 52 to focus UV light emitted by UV light source 20 inside holder 19 on reflector 49. Reflector 49 is configured cylindrically to reflect light passing through slit 52 back to slit 52 into holder 19.

Figure 10:
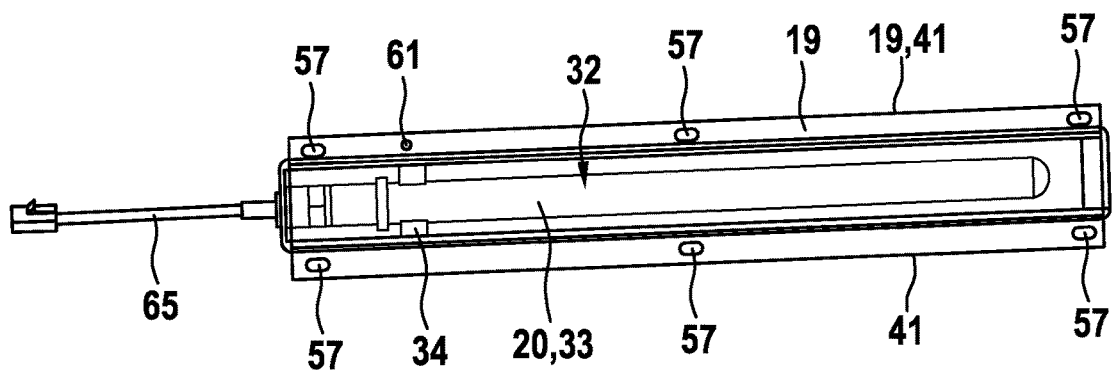
FIG. 10: shows a first perspective holder with a UV light source.
Figure 11:
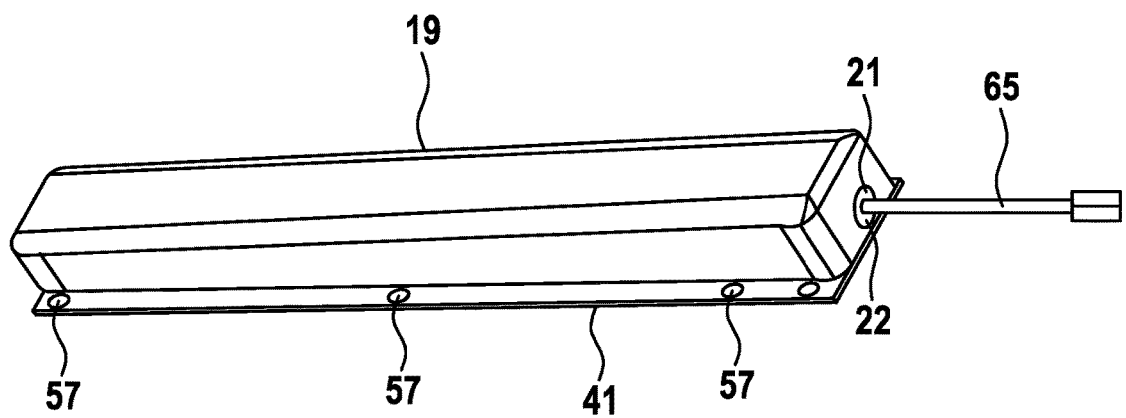
FIG. 11: shows a second perspective holder with a UV light source.

FIGS. 10 and 11 show holder 19, In FIG. 10 holder 19 is shown from an underside. A bulb 33 of a UV light source 20 is held in interior space 32 of holder 19 with clip 34. Flanges 41 of holder comprise keyholes 57 and hole 61 for a fixing member such as a screw. FIG. 10 is a further perspective view of holder 19 showing the tapered configuration of holder 19, Holder 19 comprises a pass-through wire 65 passing through hole 21 to provide UV light source 20 with electric power. Hole 21 is sealed with through-hole fitting 22.

Referring to FIG. 4, holder 19 comprises a foam 62 incorporated in wall 35 for thermal insulation of holder 19. In addition, a seal 63 is disposed between a contact surface 64 of flange 41 of holder 19 and the outer face 38 of sidewall 18 of irradiation chamber 16.

Figure 12:
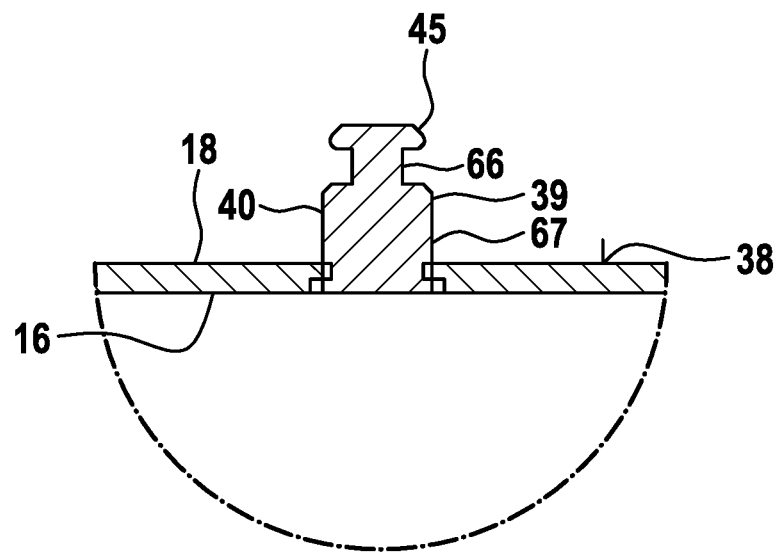
FIG. 12: shows a side view of a first mounting member configured as a stud.

FIG. 12 shows a side view of a first mounting member 40 on sidewall 18 of irradiation chamber 16. The first mounting member 40 is configured as a stud 39 comprising a head 45 and a neck part 66. The neck part 66 has a smaller diameter than the head 45. Neck part 66 is positioned between head 45 and a base part 67 of stud 39. Stud 39 protrudes from outer face 38 of the sidewall 18 at a right angle.

Figure 13:
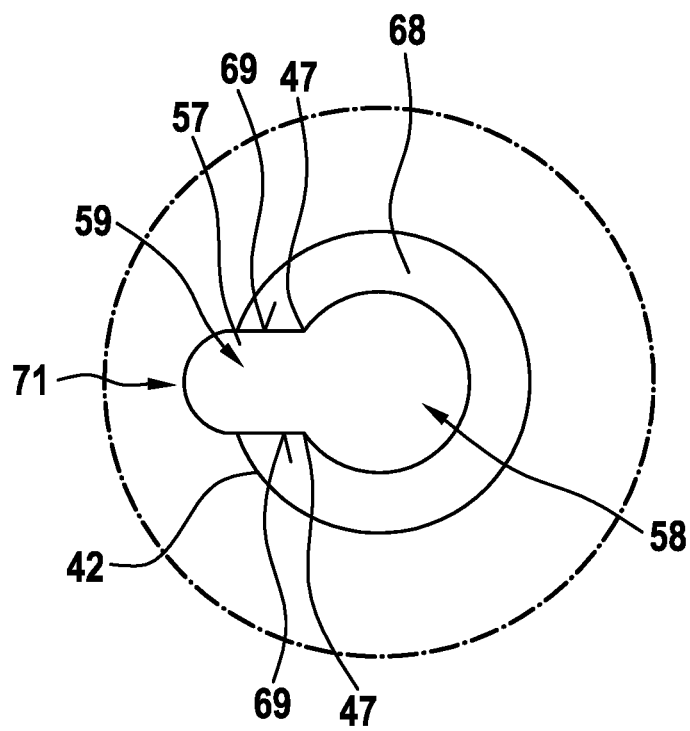
FIG. 13: shows a top view of a second mounting member configured as a keyhole.

FIG. 13 is a top view of one of the second mounting members 42 in flanges 41 of holder 19 as shown in FIG. 7. Second mounting member 42 is configured as a keyhole 57 comprising an entry section 58 and a slide section 59. Slide section 59 is located directly adjacent to entry section 58. Entry section 58 is configured essentially circularly and has a diameter, which is only slightly larger than the diameter of the head 45 of stud 39 in FIG. 12. Entry section 58 of keyhole 57 is configured as a countersunk opening 68. Due to the countersunk configuration, slide section 59 comprises inclined planes 69 at its boundary 47.

Figure 14:
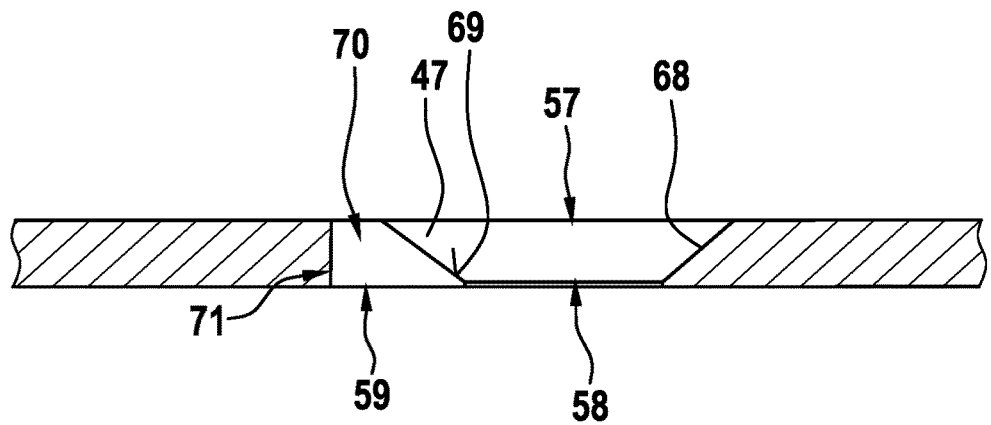
FIG. 14: shows a cross sectional view of a second mounting member configured as a keyhole.

Inclined plane 69 is better shown in FIG. 14, which is a cross sectional view of the keyhole 57 of FIG. 13. Entry section 58 is configured as countersunk opening 68. Due to the countersunk configuration, slide section 59 comprises an inclined plane 69 at its boundary 47. Because of the inclined plane 69 at the boundary 47 the thickness of the material 70 bounding slide section 59 increases from the entry section 58 in the direction from the entry section 58 to the distal end 71 of the slide section 59.

Figure 16:
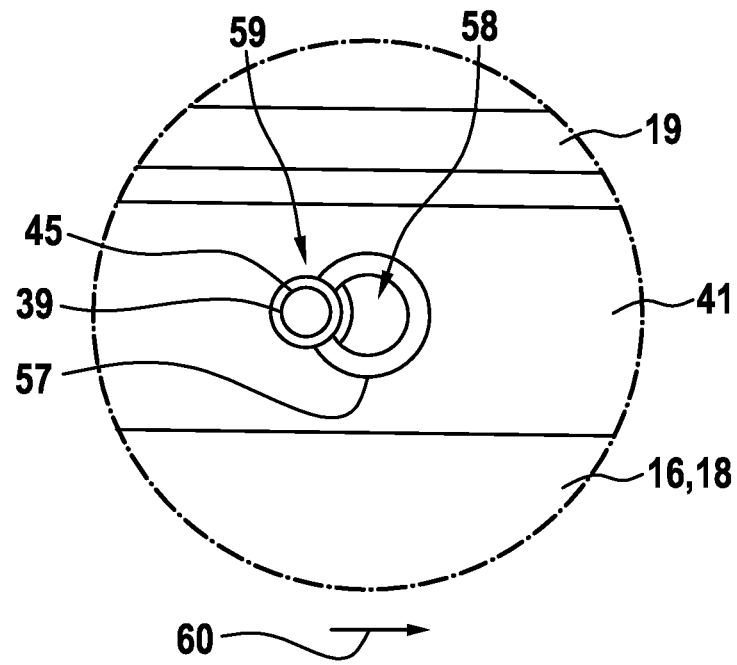
FIG. 16: shows a top view of a head of a stud engaging behind a boundary of a slide section of a keyhole.
Figure 17:
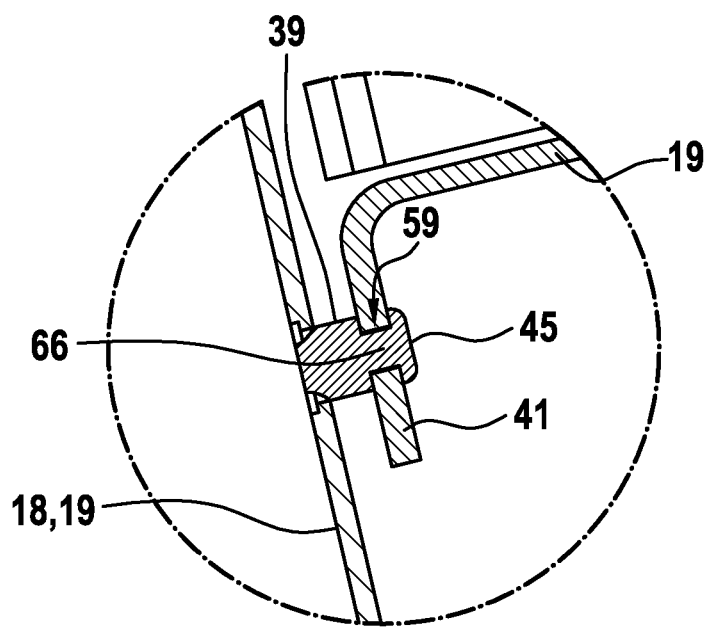
FIG. 17: shows a side view of a head of a stud engaging behind a boundary of a slide section of a keyhole.

The method for pre-mounting holder 19 to sidewall 18 of irradiation chamber 16 is described with reference to FIGS. 15 to 17.

Figure 15:
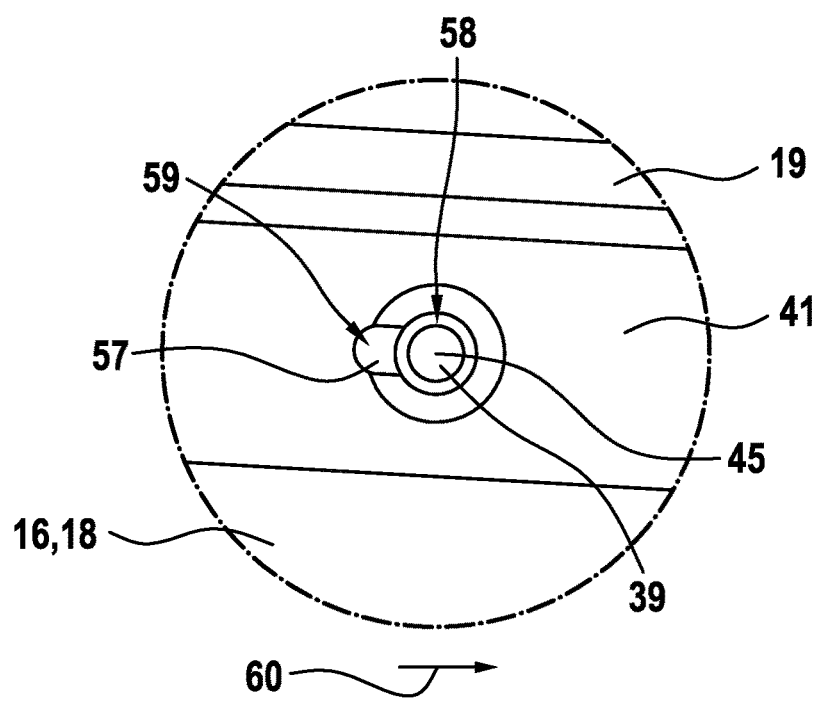
FIG. 15: shows a top view of a head of a stud guided through an entry section of a keyhole.

FIG. 15 shows a top view of one of the keyholes 57 in flange 41 of holder 19. For pre-mounting holder 19 to sidewall 18 of irradiation chamber 16, first, holder 19 is aligned with sidewall 18 in such a way, that entry section 58 of keyhole 57 is aligned with head 45 of stud 39. By approaching holder 19 to sidewall 18, head 45 of stud 39 is guided through entry section 58, so that the position shown in FIG. 15 is obtained. In a second step, holder 19 is displaced in the lateral direction 60.

In this lateral displacement of holder 19 comprising keyholes 57, neck part 66 (FIGS. 12 and 17) of each stud 39 enters the slide section 59 of the corresponding keyhole 57, while head 45 simultaneously engages behind inclined plane 69 of the slide section 59 (FIG. 14). The interaction of inclined plane 69 and head 45 creates a mechanical advantage to pre-mount holder 19 to irradiation chamber 16. The relative position of head 45 of stud 39 and keyhole 57 after the displacement of holder 19 in the lateral direction 60 is shown in a top view in FIG. 16 and in a side view in FIG. 17.

For final mounting holder 19 to sidewall 18 of irradiation chamber 16 a screw is guided through hole 61 (FIG. 7) in flange 41 of holder 19. The screw is received in a corresponding threaded hole in sidewall 18 of irradiation chamber 16. By tightening the screw, holder 19 is fixed to or immobilized at sidewall 18.

REFERENCE SIGNS

100 Device
10 Casing
11 Front door
12 Sample Chamber
13 Oscillating Board
14 Panel
15 Side Panel
16 Irradiation Chamber
17 Refrigeration or heating module
18 Sidewall
19 Holder
20 IN light source
21 Hole
22 Through-hole fitting
23 Shelf
24 Wall
25 Heat exchanger
26 Entry opening
27 Exit opening
28 Fan
29 Gratings
30 Outer fan
31 Airflow
32 Interior space
33 Bulb
34 Clip
35 Wall
36 Screw connection
37 UVC light sensor
38 Outer face
39 Stud
40 First mounting member
41 Flange
42 Second mounting member
43 Aperture
44 Protrusion
45 Head
46 Section
47 Boundary
48 Interior
49 Reflector
50 Inner face
51 Distance piece
52 Slit
53 First lateral edge
54 Second lateral edge
55 Passageway
56 Cover
57 Keyhole
58 Entry section
59 Slide section
60 Lateral direction
61 Hole
62 Foam
63 Seal
64 Contact surface
65 Pass-through wire
66 Neck part
67 Base part
68 Countersunk opening
69 Inclined plane
70 Material
71 Distal end

The invention claimed is:

1. A device for storing, incubating or manipulating biological samples, comprising a sample chamber, an irradiation chamber, and a holder with a UV light source, wherein the holder mounted to an outer face of the sidewall of the irradiation chamber, wherein a sidewall of the irradiation chamber comprises a first mounting member and wherein the holder comprises a second mounting member configured to interact with the first mounting member for pre-mounting the holder to the sidewall, wherein at least one of the sidewall of the irradiation chamber and the holder comprises a slit for focusing light from the UV light source into the irradiation chamber, wherein the irradiation chamber includes in an interior a reflector for reflecting UV light from the UV source, wherein the reflector has a cylindrical configuration, and wherein the slit is positioned in a central axis of the cylindrical configuration of the reflector, so that UV light from the UV light source entering the irradiation chamber through the slit is reflected by the reflector back onto the slit, thereby preventing or minimizing UV light being scattered through the irradiation chamber and entering the sample chamber, wherein the reflector and an inner face of the sidewall of the irradiation chamber define a passageway for air, and wherein the passageway for air is configured such that either all or at least part of an air flow in the irradiation chamber flows through the passageway for disinfection of all or part of the air.

2. The device of claim 1, wherein the first mounting member and the second mounting member are configured for fixing and immobilizing the holder to the sidewall.

3. The device of claim 1, wherein the holder is a box.

4. The device of claim 1, wherein the holder is thermally insulated.

5. The device of claim 1, wherein the first mounting member is a stud, and wherein the second mounting member is an aperture for receiving the stud.

6. The device of claim 5, wherein the stud comprises a protrusion configured to engage behind at least a section of a boundary of the aperture.

7. The device of claim 5, wherein the aperture is a countersunk aperture.

8. The device of claim 6, wherein the section of the boundary of the aperture comprises an inclined plane configured such that a relative movement of the inclined plane and the protrusion engaging behind the inclined plane creates a mechanical advantage to tighten the holder against the sidewall.

9. The device of claim 5, wherein the aperture is a keyhole.

10. The device of claim 9, wherein the the keyhole has an entry section for receiving a protrusion of the stud and a slide section adjacent to the entry section, wherein a width of the slide section is smaller than a dimension of the protrusion of the stud.

11. The device of claim 10, wherein the stud and the keyhole are configured such that upon receiving the protrusion of the stud through the entry section a relative movement of the stud and the keyhole enters the stud into the slide section so that the protrusion engages behind a boundary of the slide section.

12. The device of claim 10, wherein the section of the boundary of the aperture comprising an inclined plane is a boundary of the slide section.

13. The device of claim 11, wherein the stud and the keyhole form at least one of a clip connection and a snap fit connection.

14. The device of claim 13, wherein the boundary of the slide section at a distal end from the entry section comprises an indentation for receiving at least part of the protrusion to form the clip connection or snap fit connection.

15. The device of claim 1, further comprising a fixing member configured for fixing and immobilizing the holder to the irradiation chamber.

16. The device of claim 15, wherein the fixing member is a screw, wherein the holder comprises a hole and wherein the sidewall comprises a threaded hole for receiving the screw.

17. The device of claim 1, wherein a seal is arranged between a contact surface of the holder and the sidewall of the irradiation chamber.

18. The device of claim 17, wherein the seal is at least one of a foam seal, a urethane seal and a self-lubricating seal.

19. The device of claim 16, wherein the reflector is mounted to an inner face of the sidewall by at least one distance piece.

20. The device of claim 1, wherein at least one lateral edge of the reflector is at a distance from the inner face of the sidewall for forming at least one of an entry and an exit for air into or out of the passageway.

21. The device according to claim 5, wherein the stud is a pin, a peg or a standoff.

22. The device according to claim 6, wherein the protrusion is a head.

23. The device according to claim 10, wherein the entry section is a circular entry section.

24. The device according to claim 11, wherein the relative movement of the stud and the keyhole enters a neck part of the stud into the slide section.

25. The device according to claim 1, wherein the device is an incubating device or shaking device.

* * * * *